(12) United States Patent
Hostettler et al.

(10) Patent No.: US 11,883,637 B2
(45) Date of Patent: Jan. 30, 2024

(54) INJECTION DEVICE HAVING A THREAD HAVING A VARIABLE PITCH

(71) Applicant: Ypsomed AG, Burgdorf (CH)

(72) Inventors: Patrick Hostettler, Hasle (CH); Markus Tschirren, Burgdorf (CH)

(73) Assignee: Ypsomed AG, Burgdorf (CH)

( * ) Notice: Subject to any disclaimer, the term of this patent is extended or adjusted under 35 U.S.C. 154(b) by 331 days.

(21) Appl. No.: 17/064,298

(22) Filed: Oct. 6, 2020

(65) Prior Publication Data
US 2021/0016016 A1 Jan. 21, 2021

Related U.S. Application Data

(63) Continuation of application No. 15/850,171, filed on Dec. 21, 2017, now Pat. No. 10,799,647, which is a (Continued)

(51) Int. Cl.
*A61M 5/31* (2006.01)
*A61M 5/315* (2006.01)
(Continued)

(52) U.S. Cl.
CPC ...... *A61M 5/31581* (2013.01); *A61M 5/1454* (2013.01); *A61M 5/20* (2013.01);
(Continued)

(58) Field of Classification Search
CPC .............................. A61M 5/20; A61M 5/2033
See application file for complete search history.

(56) References Cited

U.S. PATENT DOCUMENTS

| 5,320,609 A * | 6/1994 | Haber ............... A61M 5/31551 604/137 |
| 2007/0244436 A1* | 10/2007 | Saiki .................. A61M 5/3158 604/134 |

(Continued)

FOREIGN PATENT DOCUMENTS

| EP | 2692377 A1 | 2/2014 |
| EP | 2542280 B1 | 7/2014 |

(Continued)

OTHER PUBLICATIONS

"International Preliminary Report on Patentability for Application No. PCT/CH2016/000084", dated Dec. 26, 2017, 8 pages.

(Continued)

*Primary Examiner* — Courtney B Fredrickson
(74) *Attorney, Agent, or Firm* — Dorsey & Whitney LLP

(57) ABSTRACT

An autoinjector for dispensing a liquid product, in particular a highly viscous medication, includes: a housing, a product container, which is arranged in the housing and has a slidable piston, wherein the piston can be slid in a dispensing direction in order to dispense the product contained in the product container, a forward drive element, which acts on the piston as the product is being dispensed, a first spring, which is preloaded such that the product can be dispensed from the product container by the sliding of the forward drive element and the piston, and a rotation element, which is operatively coupled to the forward drive element, wherein the first spring acts on the rotation element in such a way that the rotation element is set into rotation in order to dispense the product, wherein the rotation element or the forward drive element has a thread having a variable pitch.

18 Claims, 8 Drawing Sheets

Related U.S. Application Data continuation of application No. PCT/CH2016/000084, filed on Jun. 1, 2016.

(51) Int. Cl.
- *A61M 5/20* (2006.01)
- *A61M 5/32* (2006.01)
- *A61M 5/145* (2006.01)
- *A61M 5/46* (2006.01)
- *A61M 5/48* (2006.01)

(52) U.S. Cl.
CPC ........ *A61M 5/2033* (2013.01); *A61M 5/3157* (2013.01); *A61M 5/3159* (2013.01); *A61M 5/31583* (2013.01); *A61M 5/31585* (2013.01); *A61M 5/31586* (2013.01); *A61M 5/3204* (2013.01); *A61M 5/326* (2013.01); *A61M 5/46* (2013.01); *A61M 5/484* (2013.01); *A61M 2005/202* (2013.01); *A61M 2005/2013* (2013.01); *A61M 2005/2086* (2013.01); *A61M 2005/3143* (2013.01); *A61M 2005/3152* (2013.01); *A61M 2005/3247* (2013.01); *A61M 2005/3267* (2013.01); *A61M 2205/3341* (2013.01); *A61M 2205/581* (2013.01); *A61M 2205/582* (2013.01); *A61M 2207/00* (2013.01)

(56) References Cited

U.S. PATENT DOCUMENTS

| | | | | |
|---|---|---|---|---|
| 2013/0112521 A1* | 5/2013 | Ekman | ............... | A61M 5/46 |
| | | | | 192/69.8 |
| 2013/0131602 A1* | 5/2013 | Kemp | ............... | A61M 5/3202 |
| | | | | 604/197 |
| 2013/0245558 A1* | 9/2013 | Holmqvist | ......... | A61M 5/31585 |
| | | | | 604/211 |
| 2014/0350481 A1 | 11/2014 | Raab et al. | | |
| 2016/0271332 A1* | 9/2016 | Bilton | ............... | A61M 5/31551 |
| 2018/0110926 A1 | 4/2018 | Schrul et al. | | |
| 2018/0169346 A1 | 6/2018 | Hostettler et al. | | |

FOREIGN PATENT DOCUMENTS

| | | | | |
|---|---|---|---|---|
| EP | 2881131 A1 | 6/2015 | | |
| WO | 2007115424 A1 | 10/2007 | | |
| WO | WO-2009146996 A1 * | 12/2009 | ......... | A61M 5/3135 |
| WO | 2014111370 A1 | 7/2014 | | |
| WO | 2014146210 A1 | 9/2014 | | |
| WO | 2014154491 A1 | 10/2014 | | |
| WO | 2014166887 A1 | 10/2014 | | |
| WO | 2014166914 A1 | 10/2014 | | |
| WO | 2014170267 A1 | 10/2014 | | |
| WO | 2014191189 A1 | 12/2014 | | |
| WO | 2015/032455 A1 | 3/2015 | | |
| WO | 2015055642 A1 | 4/2015 | | |
| WO | 2016007800 A1 | 1/2016 | | |
| WO | 2016071483 A1 | 5/2016 | | |

OTHER PUBLICATIONS

"International Preliminary Report on Patentability for Application No. PCT/CH2016/000093", dated Dec. 26, 2017, 7 pages.

"International Search Report for Application No. PCT/CH2016/000084", dated Jul. 12, 2016, 3 pages.

"International Search Report for Application No. PCT/CH2016/000093", dated Aug. 5, 2016, 3 pages.

* cited by examiner

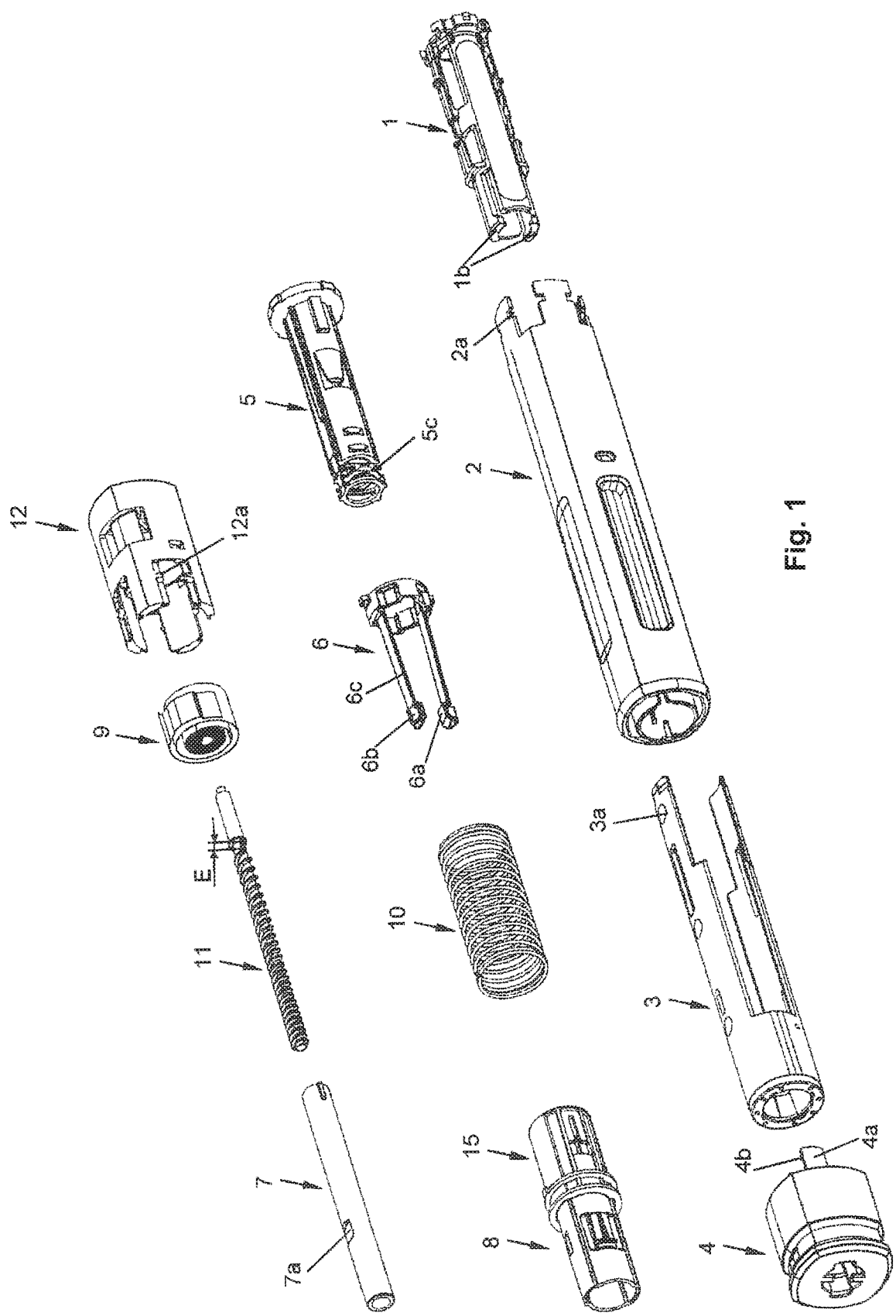

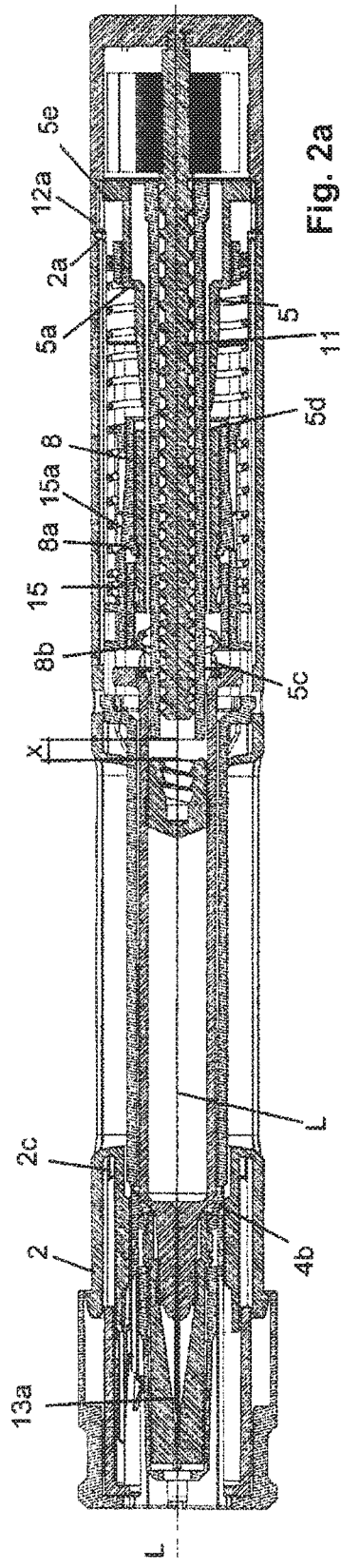
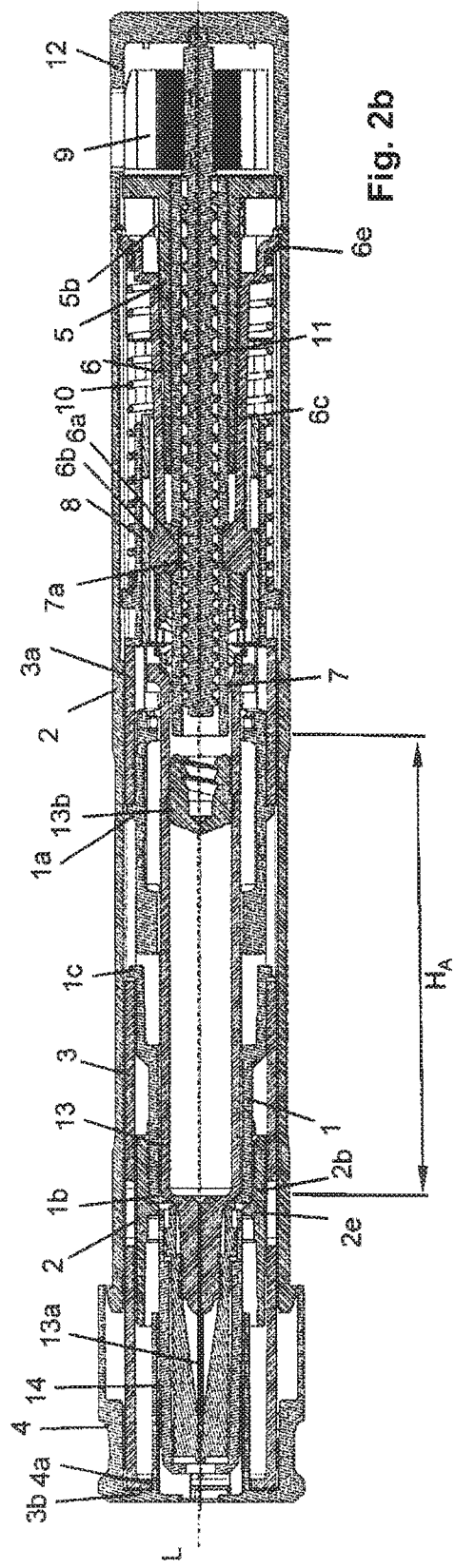
Fig. 2a
Fig. 2b

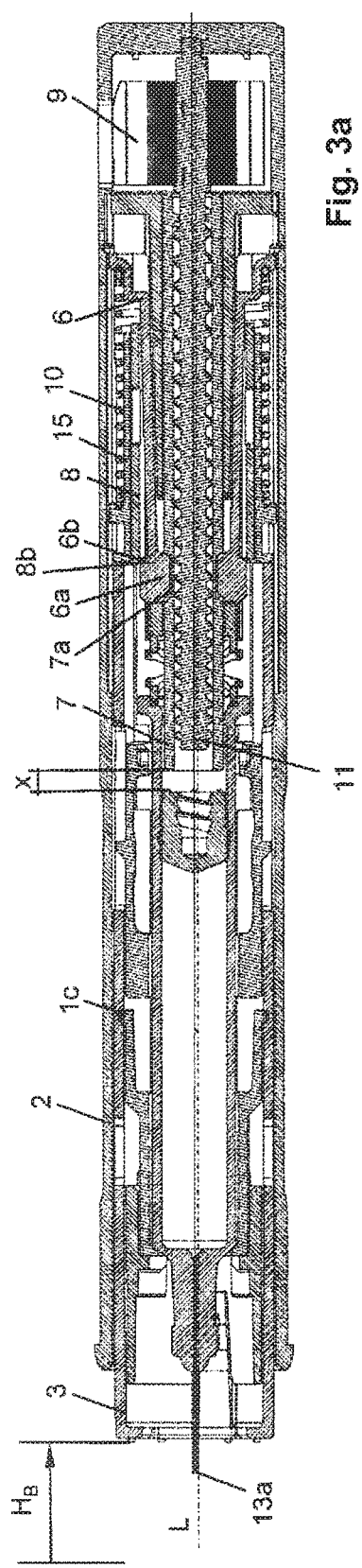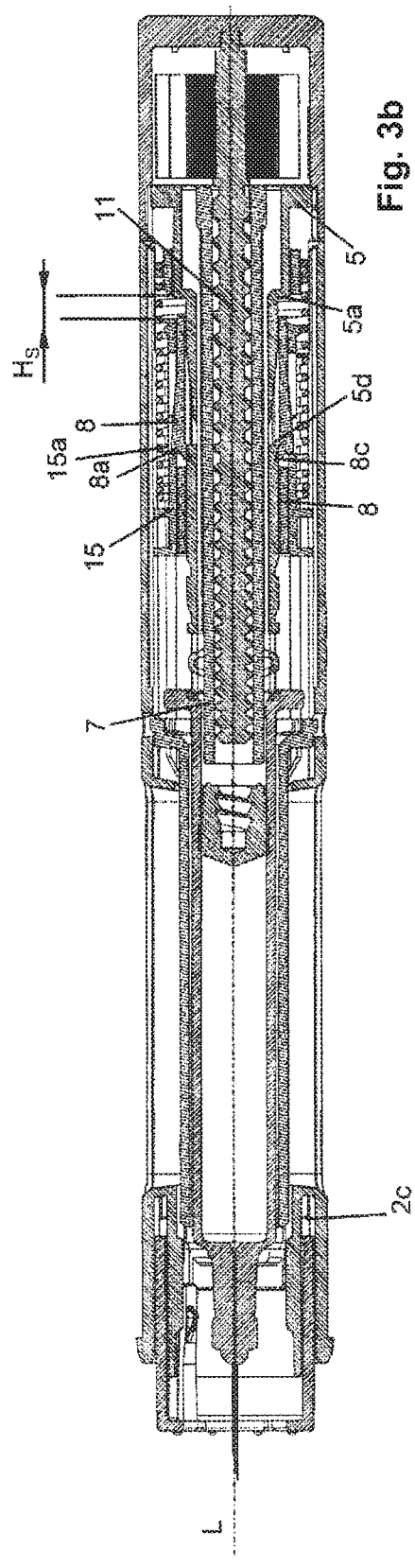

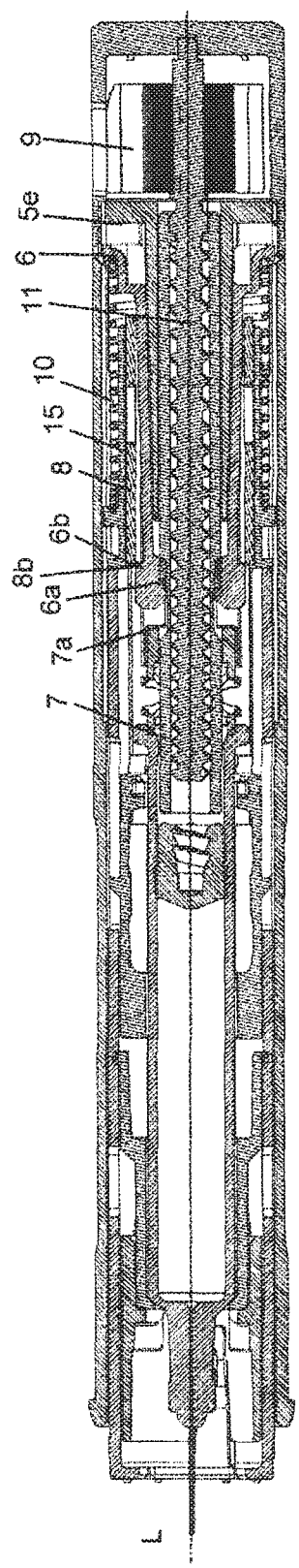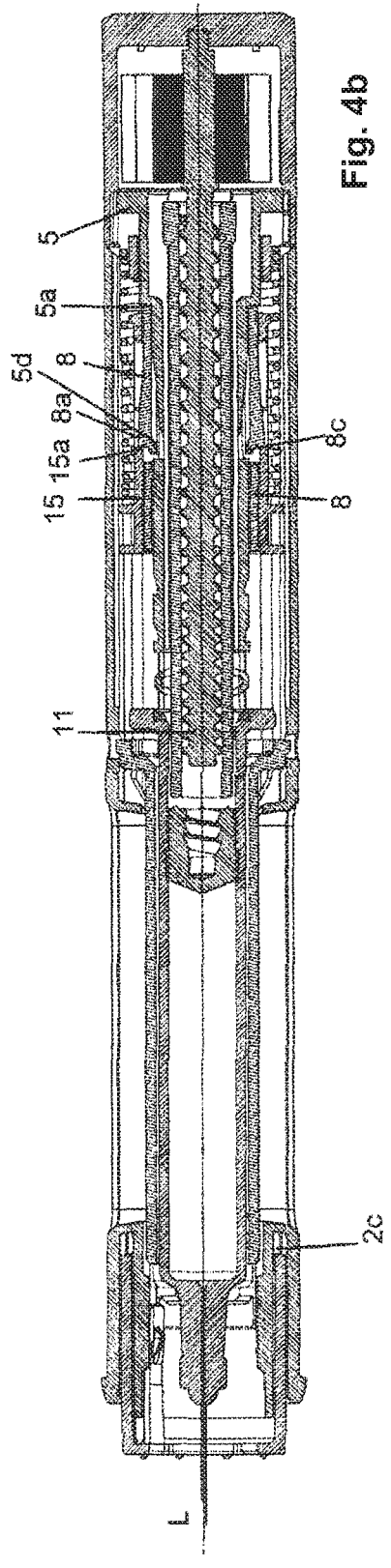

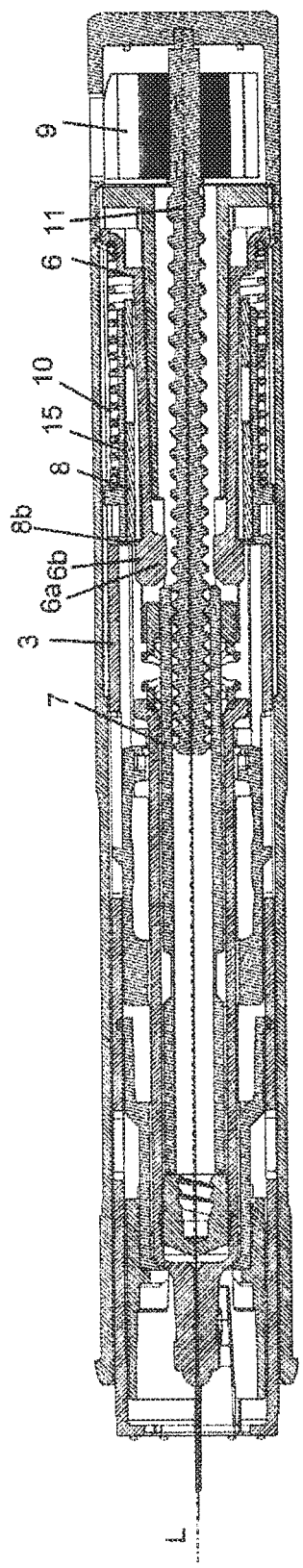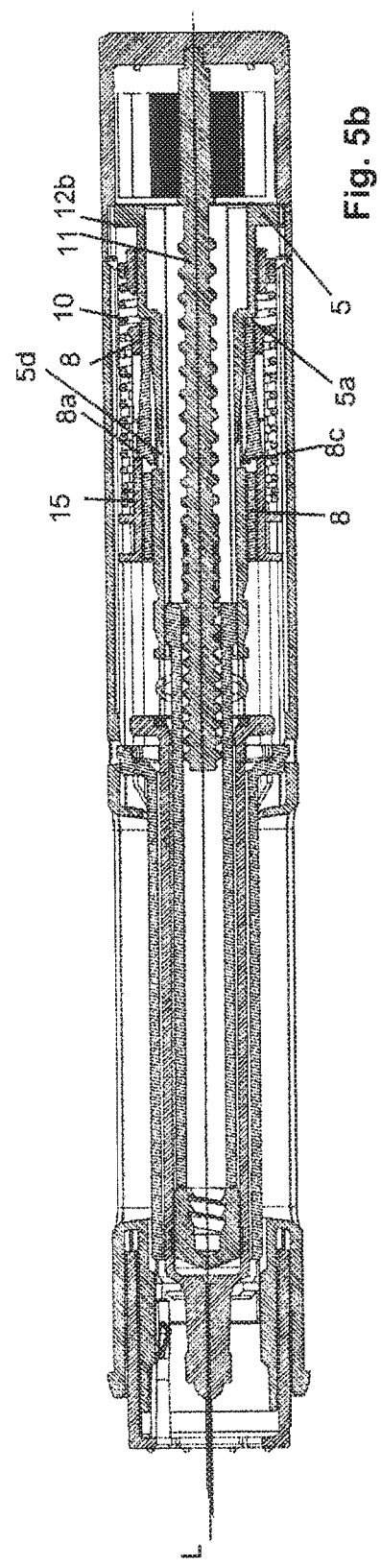

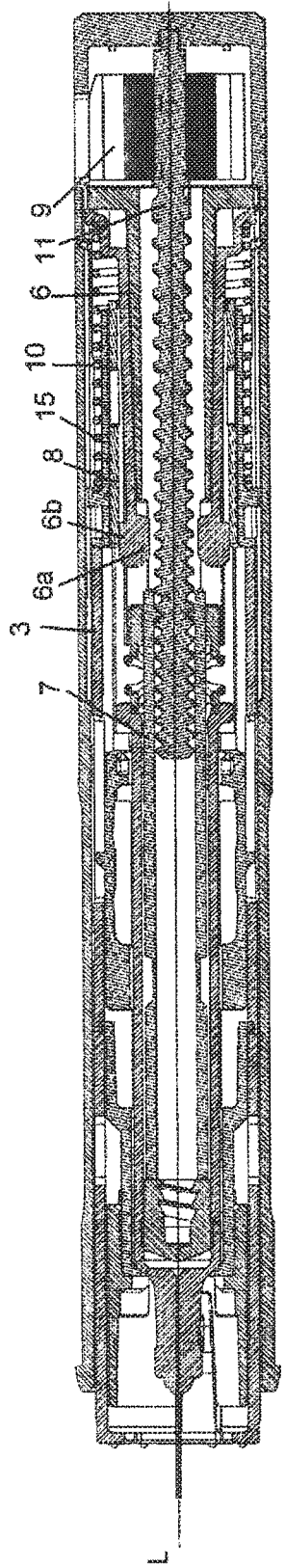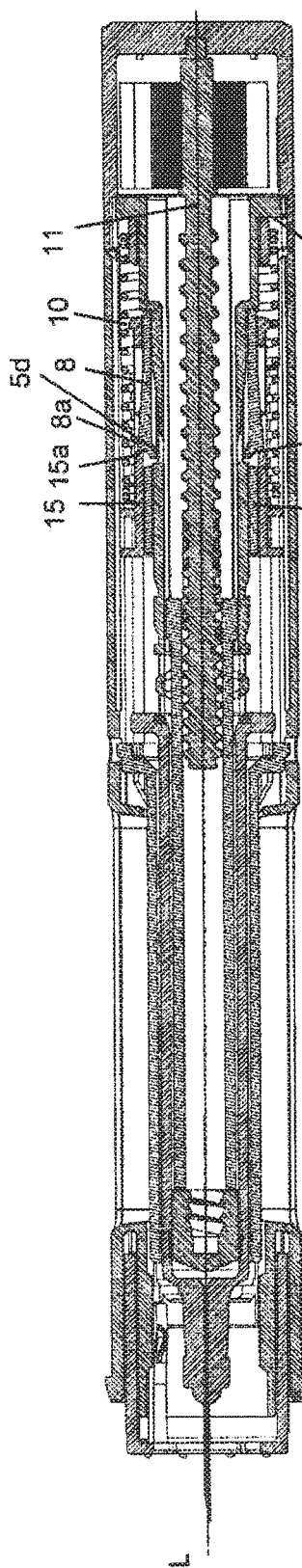

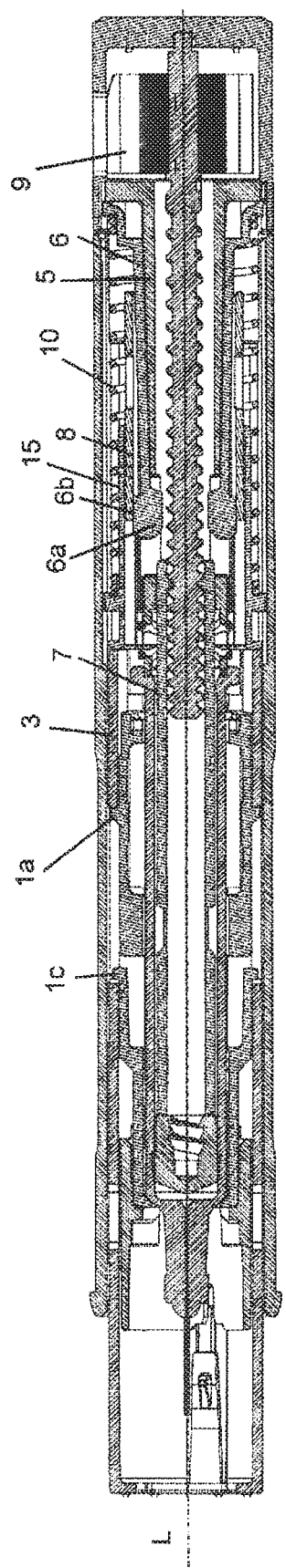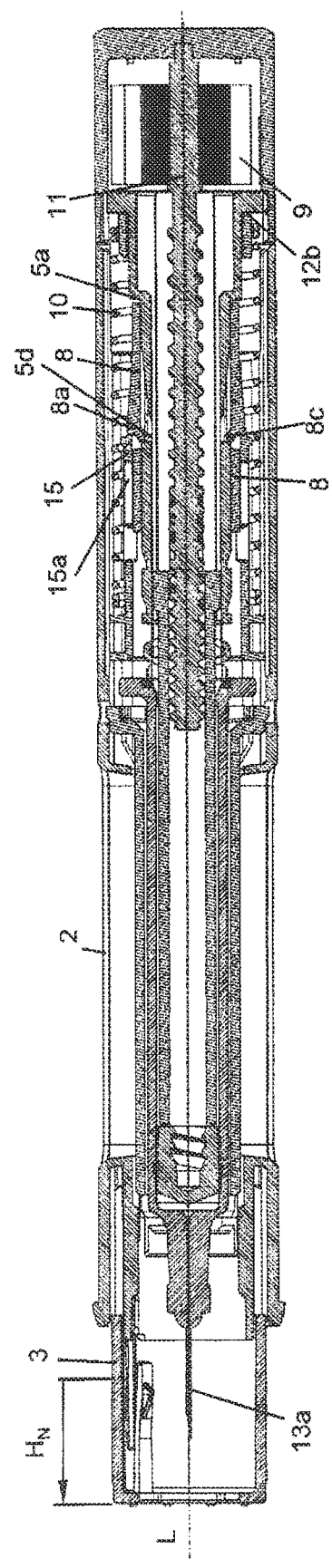

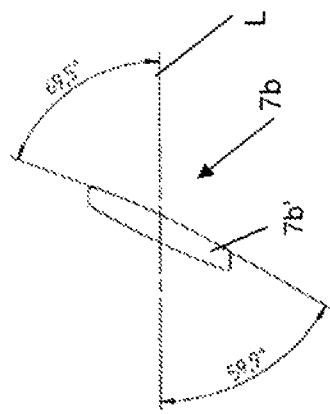
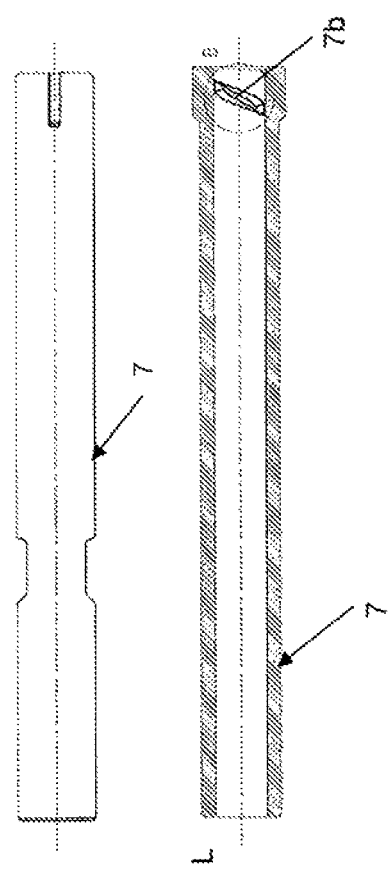
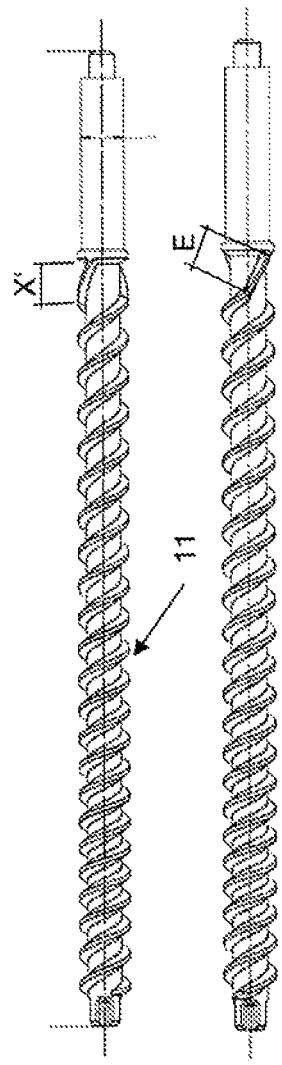
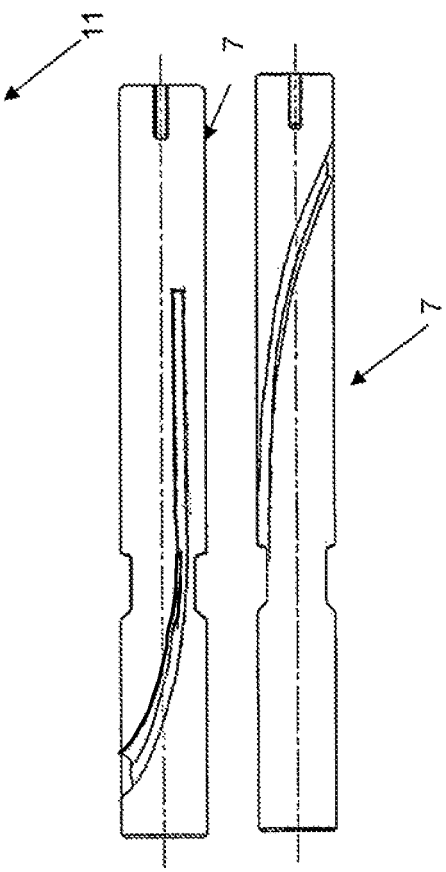
Fig. 8a
Fig. 8b
Fig. 8c

INJECTION DEVICE HAVING A THREAD HAVING A VARIABLE PITCH

CROSS-REFERENCE TO RELATED APPLICATIONS

This application is a continuation U.S. patent application Ser. No. 15/850,171 filed on Dec. 21, 2017, issued as U.S. Pat. No. 10,799,647 on Oct. 13, 2020, which in turn is a continuation of International Application No. PCT/CH2016/000084 filed Jun. 1, 2016, which claims priority to Swiss Application No. 904/15 filed Jun. 23, 2015, the contents of all of which are herein incorporated by reference.

BACKGROUND

The invention relates to an injection device for administering a liquid product, particularly a highly viscous medicine; more particularly, the invention relates to a driving and signal device and to a method for such an injection device.

The term "medicine" or product comprises any flowable medical formulation that is suitable for controlled administration by a means such as a cannula or a hollow needle, the term comprising, for example, a liquid, a solution, a gel or a fine suspension that contains one or more medically active substances. A medicine can be a composition having a single active ingredient or a premixed or co-formulated composition having multiple active ingredients, from a single container. Medicine or product comprises pharmaceuticals such as peptides (e.g. insulin, and insulin-containing medicines, preparations containing GLP-1 and derived or analogous substances), proteins and hormones, biologically obtained or active substances, substances based on hormones or genes, nutritional formulations, enzymes and additional substances, both in solid (suspended) or liquid form, but also polysaccharides, vaccines, DNA or RNA or oligonucleotides, antibodies or parts of antibodies as well as suitable base, auxiliary and carrier substances.

From the prior art, WO2014146210, an injection device is known, more particularly an autoinjector with an automatic piercing process, an automatic dispensing process and a signal device, wherein the energy for piercing, dispensing and for the signal device is supplied by the piercing and dispensing spring. During the dispensing, the piercing and dispensing spring is coupled to a drive nut, whereby a thread-like piston rod is set into rotation and displaced in the axial direction. The spring torque in this case diminishes during the dispensing and in particular, toward the end of the dispensing. That is to say, dispensing is done with less force toward the end of the piercing and injection movement than at the beginning.

SUMMARY OF THE INVENTION

A problem addressed by the invention is that of specifying an injection device that has an apparatus for dispensing highly viscous medicines.

This problem is solved by the autoinjector according to claim 1. Advantageous developments can be derived from the dependent claims, the description and the appended figures.

An autoinjector for dispensing a liquid product, in particular a highly viscous medicine, comprising: a housing and a product container having a displaceable piston and arranged in the housing, wherein the piston can be displaced in a dispensing direction to dispense the product contained in the product container, a drive member, which acts on the piston during product dispensing, and a first spring, which is preloaded so that the product can be dispensed from the product container by displacement of the drive member and the piston, characterized by a rotation member or threaded rod that is operatively coupled to the drive member, wherein the first spring acts on the rotation member such that the rotation member is set into rotation to dispense the product, wherein the rotation member or the drive member has a thread having a variable pitch.

Either the drive member has at least one thread segment and has a threaded connection to the rotation member, or the rotation member has at least one thread segment and has a threaded connection to the drive member.

A flank of the at least one thread segment of the drive member or the rotation member has different pitch angles.

The rotation member has a thread start having an axial portion, and between the drive element and the piston there is a distance, in particular an acceleration path, wherein the axial portion is larger than the acceleration path.

The thread having the variable pitch has at least one region having a continuous pitch variation or/and the pitch variation of the thread having the variable pitch is discontinuous, at least in certain regions.

The thread having the variable pitch has a degressive thread pitch, whereby the decrease of the spring torque during the dispensing can be compensated.

In a helical movement between the threaded rod and the at least one thread segment of the drive member, the flank of the at least one thread segment is screwed on the thread having the variable pitch of the threaded rod, wherein different regions of the flank contact the thread having the variable pitch.

The drive member has a first threaded connection to the rotation member and a second threaded connection to the housing or an element fixed relative to the housing.

The first spring is a spiral spring.

The threaded rod is mounted axially fixedly in the housing and is coupled to the first spring in such a manner that a relaxation of the first spring leads to rotation of the threaded rod and that the drive member is rotationally fixed relative to the housing.

In a storage position, the axial forces, which arise particularly due to a thread transmission from the torque of the spring, are kept small in that, in the storage position, the thread having the variable pitch has a threaded connection at a point having a large pitch.

A retaining element has at least one axially directed arm, and a first engagement element and a second engagement element are positioned on the at least one arm, and the first engagement element releasably engages with a recess of the drive member, whereby the drive member is coupled axially fixedly to the retaining element, wherein the coupling between the drive member and the retaining element is released when the retaining element is disengaged from the drive member, wherein the drive member is prevented by the engagement from moving in the dispensing direction relative to the retaining element, wherein this engagement of the first engagement element can be released for product dispensing, so that the first spring can drive the drive member in the dispensing direction relative to the retaining element.

The drive member can be moved by means of the first spring in the distal direction relative to the retaining element when the first engagement member is disengaged from the drive member and the second engagement member is engaged with the needle guard sleeve or a switching module.

The retaining element is engaged with a drive member and/or with the switching module.

Method for multiple use of a retaining element in an autoinjector, containing at least two of the following steps: retaining the drive member by means of the retaining element, and/or axial movement of the retaining element to produce a start click signal, and/or axial movement of the retaining element to produce an end click signal.

Additional Aspects of the Invention can Include:

The switching module has a switching sleeve and a blocking sleeve, wherein the blocking sleeve has a latching element that operates unidirectionally and that engages with the switching sleeve, wherein the switching sleeve, in the movement thereof in the proximal direction relative to the housing, drives the blocking sleeve via the latching member and, during the movement of the switching sleeve in the proximal direction relative to the housing, the switching sleeve is displaced relative to the blocking sleeve into an additional blocking position, in which the latching member blocks a movement of the switching sleeve in the proximal direction relative to the blocking sleeve, wherein the retaining element engages by means of at least one second engagement element with the blocking sleeve.

The switching module is arranged kinematically and/or geometrically between a second spring and the needle guard sleeve, wherein the switching module is driven by the needle guard sleeve in the proximal direction when the needle guard sleeve is displaced in the proximal direction from its initial position.

The retaining element having the first engagement element is engaged with the drive member before initiating the product dispensing, whereby the drive member is prevented from moving in the dispensing direction relative to the retaining element, wherein this engagement of the first engagement element can be released for product dispensing so that the first spring can drive the rotation element and can displace the drive element in the dispensing direction relative to the retaining element.

The autoinjector has a start signal stop and the second spring, which exerts a spring force on the retaining element acting oppositely to the dispensing direction, wherein the retaining element is coupled to the drive member, and wherein the axially fixed coupling between retaining element and drive member can be released and the retaining element can be accelerated by means of the second spring opposite to the dispensing direction and relative to the drive member and/or the housing.

The retaining element having the second engagement element, which can be moved by the disengaging movement of the first engagement element out of the drive member into an axially fixed engagement with the needle guard sleeve or the switching module, in particular into the blocking sleeve, wherein the retaining element, decoupled from the axially fixed coupling and accelerated by the second spring, moves the blocking sleeve to a start signal stop and strikes against the start signal stop, whereby an acoustic and/or tactile start signal is generated.

The drive member prevents the second engagement member from disengaging from the engagement with the blocking sleeve when the drive member moves in the distal direction relative to the retaining element, wherein the drive member, at the end of the dispensing stroke ($H_A$), allows the engagement member to disengage from the engagement with the blocking sleeve, whereby the retaining element is accelerated by the second spring contrary to the dispensing direction and strikes against an end signal stop, whereby an acoustic and/or tactile end signal is generated.

The end signal stop of the housing or of an element such as the mechanism holder, which is connected at least axially fixedly, preferably also rotationally fixedly, to the housing.

The retaining element having the second engagement member, which can be moved by the disengaging movement of the first engagement member from the drive member into an axially fixed engagement with the needle guard sleeve or the switching module, wherein the first engagement member and the second engagement member are matched to one another in such a manner that the second engagement member already engages axially fixedly with the needle guard sleeve when the first engagement member has not yet completely released from the engagement with the drive member.

A needle guard sleeve, which can be displaced in order to initiate the product dispensing from the initial position thereof relative to the housing and along the longitudinal axis of the autoinjector in the proximal direction, in particular by an actuation stroke, whereby the second spring is loaded and in particular product dispensing is initiated.

After dispensing product, in particular when the drive member has been displaced by the dispensing stroke in the distal direction, the needle guard sleeve can be displaced by the second spring relative to the housing in the distal direction, in particular by a needle guard stroke (Hs), into a needle guarding position in which the needle guard sleeve extends past the needle tip of an injection needle of the product container.

A latching member, which locks the needle guard sleeve in the needle guarding position thereof relative to the housing against being pushed back in the proximal direction, at least in such a manner that the needle tip cannot exit from the distal end of the needle guard sleeve.

The autoinjector according to the invention has a housing and a product container arranged in the housing. The product container is, in particular, a syringe or a carpule that has a container body, at the distal end of which an injection needle is either fixedly arranged or can be attached. The container body surrounds a piston that can be displaced in relation to the syringe body and is displaced toward the distal end for product dispensing, whereby the liquid product arranged between the piston and the injection needle, in particular a highly viscous medicine, is dispensed through the injection needle out of the product container. The syringe body can have a flange, which can also be referred to as a finger flange, at the proximal end thereof, i.e. the rear end or the end opposite the injection needle. A syringe constructed in this manner can be obtained as a standard syringe, so that a specially adapted syringe need not be used for the autoinjector. The piston tightly contacts the inner diameter of the syringe body.

The housing is preferably elongated and forms the longitudinal axis of the autoinjector. The housing is preferably sleeve-shaped and/or cylindrical. For example, the container can be displaceably arranged in the housing, i.e. displaceable in the distal direction relative to the housing for automatic piercing, so that the needle tip exits from an opening at the distal end of the autoinjector and can automatically be inserted into the patient's body. In such a device, the needle tip can optionally be moved into the distal end of the device after product dispensing is finished, in particular the product container can be moved in the proximal direction relative to the housing.

In preferred embodiments, the product container is received non-displaceably along the longitudinal axis in the housing, more particularly by means of a product container holder or a syringe holder, which holds the product container axially fixedly and is axially fixedly connected to the housing, in particular interlocked therewith. The needle tip preferably protrudes in the distal direction past the distal end of the housing. In this way the needle can be inserted into the patient's body at the puncture point by means of a movement of the housing. A needle guard sleeve that forms the distal end of the autoinjector and has an opening for the injection needle is preferably provided, wherein the needle can pass through the opening. The initial position of the needle guard sleeve can be arranged in relation to the needle tip such that the needle guard sleeve extends distally past the needle tip, or the needle tip can protrude distally past the distal end of the needle guard sleeve. The needle guard sleeve can be displaced in the proximal direction relative to the housing by an actuation stroke from its initial position into an actuated position, more particularly into the housing, so that the needle emerges from the distal end and/or emerges further through the opening of the needle guard sleeve. The needle guard sleeve can preferably be displaced by a needle guard stroke from the initial position into a needle guarding position, in which the distal end of the needle guard sleeve extends distally past the needle tip in order to prevent a risk of injury that could result from an exposed needle tip after use of the device or after product dispensing has been completed. The needle guard sleeve can be displaced in the proximal direction, against the force of a spring for example, which can be designated as the needle guard spring, wherein the spring, which can be the second spring described below, for example, or a separate spring, can displace the needle guard sleeve from the actuated position in the distal direction, i.e. into the needle guarding position. The autoinjector can have a latching member, arranged resiliently for example, that locks the needle guard sleeve in the needle guarding position, particularly in relation to the housing, and blocks the needle guard sleeve from being pushed back in the proximal direction or into the housing. The latching member locks the needle guard sleeve at least in such a manner that the needle cannot emerge from the distal end of the needle guard sleeve. For example, the needle guard sleeve can be displaced from the needle guarding position in the proximal direction only to such an extent that the needle tip does not emerge from the distal end of the needle guard sleeve.

Piston Rod

The autoinjector further comprises a drive member or a piston rod that acts on the piston, more particularly bears against the piston, at least during the product dispensing, and a first spring that acts directly or indirectly on the drive member. The drive member can be sleeve-shaped, for example. The spring can be tensioned before use, e.g. as an intermediate step, or while setting a dose. The spring can preferably be already preloaded at delivery of the autoinjector with sufficient energy for dispensing multiple product doses, in particular for dispensing all the product that can be dispensed from the product container.

Rotation Member or Threaded Rod and Spring

The autoinjector can further comprise a rotation member or threaded rod, the rotation of which causes the spring energy of a spring to be output to the drive member, whereby the drive member is moved in the distal direction.

The rotation member can be connected to the spring, in particular a torsion spring or rotational spring, that stores the energy necessary for product dispensing and outputs it as needed. In principle, the spring can be helical or preferably spiral-shaped. The spring can be wound from a wire or preferably from a strip-shaped material, particularly spring steel. Spirally wound springs are also called clock springs or mainsprings.

The torque of the spring must act between the rotational member and the drive member. The spring can be connected to the rotation member or directly to the drive member and/or to any other desired element that is axially and/or rotationally fixedly mounted in the housing, or to an element that is axially and/or rotationally displaceable relative to the housing. The spring can be axially fixedly mounted in the housing, but it can also be axially displaceable relative to the housing.

For example, the rotation member can be coupled at one end to the spring, while the other end of the spring can be connected to a different element that is movable relative to the housing, in particular axially or rotationally movable. In a preferred embodiment, the other end of the spring is connected to the housing or to an element that is fixed relative to the housing.

The rotation element and/or the drive member and/or a different element coupled to the drive member can have a thread having a variable pitch, wherein the thread can have a large pitch in a first region of the thread and different-sized pitches in additional regions.

For tolerance reasons, there can be a space between the piston rod and the piston in the delivery state of the autoinjector. It is attempted during manufacture to keep the distance as small as possible, so that the impact of the piston rod on the piston does not cause breakage of glass. This distance between piston rod and piston is also called the acceleration path. In order to control or decelerate the acceleration of the piston rod in the acceleration path and minimize the risk of glass breakage, a thread start path having a large pitch, particularly on the rotation member and/or the drive member, is selected for the start of the piston rod movement. The axial portion of the thread start path is preferably larger than the acceleration path. In addition, the axial forces that arise in a storage position due to thread transmission, particularly from the spring torque due to the thread transmission, can be kept small by a large pitch.

The thread and/or the thread pitch can vary along the length of the rotation element and/or the drive element and/or the housing. The thread can have one start or multiple starts. The thread is preferably two-start. The pitch can be progressive or degressive. For example, a further region of the rotation element can have a smaller pitch than the first region, wherein the largest thread pitch can preferably not be self-locking.

With such a varying thread, it is possible to compensate for the drop of spring torque and hold the dispensing force in a constant range during the dispensing. It is possible to choose a small thread pitch at the end of the dispensing movement and thus increase the dispensing force so that a plug friction force, which can increase at the end of the dispensing, can be compensated, for example, and complete dispensing can be guaranteed. The rotation member and/or the drive member and/or the housing can have multiple regions having different thread pitches. For example, the thread can have a large thread pitch for the thread start and then a region having continuously decreasing thread pitch for slow dispensing, and end in a region having a small thread pitch in order to guarantee complete dispensing. It is of course also possible for the thread pitch to progress after the thread start from a small pitch to a large thread pitch, in order to obtain a large dispensing force at the beginning of dispensing and a small dispensing force at the end of dispensing.

The rotation of the rotation element and/or the drive element about a predetermined angle of rotation causes the drive member to advance axially by a corresponding dispensing stroke. Variable pitch angles yield variable advancements of the drive member for an identical angle of rotation. By a release of the drive member, the spring can be allowed to move the drive member in the distal direction. In particular, the rotation member can be coupled to the drive member in such a manner that the rotation element is released for a rotation relative to the housing during triggering or release of the drive member in order to dispense the product, and is blocked for rotation relative to the housing in a non-activated state of the drive member. The rotation element can preferably have an engagement with the drive member, particularly a threaded engagement, wherein the threaded engagement or the threaded nut on the drive member or the rotation member can have one or more thread segments; preferably there can be two thread segments. The thread segment is preferably selected such that a thread having a variable pitch can be rotated without impediment by the thread segments. For example, the thread segment can have a circular shape or an oval shape in a developed view; in particular, the periphery can have different angles with relation to a longitudinal axis.

A flank of the thread segments of the drive member or the rotation member can preferably have different pitch angles.

The thread segment is preferably screwed onto the thread of the rotation element with line contacts, wherein a different region of the thread segments is always in contact with the thread. In particular, in a screwing movement between the threaded rod or the drive member and the at least one thread segment of the drive member or of the threaded rod, the flank of the at least one thread segment can be screwed onto the thread of the threaded rod or the drive member that has the variable pitch, wherein different regions of the flank contact the thread having the variable pitch. During the screwing movement between the threaded rod and the drive member, the region of the threaded rod that has the largest threaded pitch is thus in contact with the region of the thread segment that has the largest pitch, or the region of the threaded rod that has the smallest thread pitch is in contact with the region of the thread segment that has the smallest pitch angle.

In an alternative example, the rotation member can have or be a threaded nut and the drive member can have or be a threaded rod, wherein the thread of the threaded nut engages with the thread of the threaded rod and, in particular, is not self-locking.

The rotation member is preferably axially fixed in relation to the housing or can at least be supported axially fixedly in one, preferably distal, direction on the housing or an element that is fixed relative to the housing such as the mechanism holder; it is also possible that the rotation element can carry out an axial stroke relative to the housing. In particular, the rotation member can be axially displaceable if the element on which the rotation element is supported also carries out an axial movement or the rotation member has a threaded connection to an element fixed relative to the housing or to an element that is axially displaceable relative to the housing.

It is also possible that multiple control cams or threads are active between different elements. The different threads can have a supplementary effect, that is to say the thread pitches for the axial path sum up with one another or subtract from one another, and thus a step-up or step-down transmission is achieved. For example, the rotation member can have a threaded connection to the drive member and the drive member can have a threaded connection to the housing or to an element fixed relative to the housing, wherein the drive member can also carry out a rotational movement. It is also possible that the rotation member has threaded connections to the drive member and to an element fixed relative to the housing, wherein these thread portions can differ from one another and can each have either variable or constant pitch regions.

The threads can each be applied to the inner side or the outer side of the rotation member and/or the drive member. All of the thread runs on the different elements can be variable, or only one of them can be variable. For example, the rotation member can have a continuously and/or discontinuously variable thread and the drive element can have a continuously and/or discontinuously variable thread pitch. The thread having the variable pitch can preferably have at least one region having a continuous pitch variation or/and the pitch variation of the thread having the variable pitch can run discontinuously, at least in certain regions.

All elements preferably have thread segments and can be selected such that the variable thread can be rotated through the thread segments without self-locking.

The threads or the thread pitches can thus run progressively or digressively. It is also possible that the thread has discontinuous pitches, i.e. regions with a different pitch. Of course the thread having the variable pitch can have regions with a continuous pitch variation or/and the variation of the thread having the variable pitch can run discontinuously, at least in certain regions.

In a preferred embodiment, the drive member is rotationally fixed relative to the housing.

Displacing the drive part by the dispensing stroke also displaces the piston. To the extent that there is a distance between the piston and the drive member in the delivered state, the dispensing stroke of the piston is smaller than the dispensing stroke of the drive member, which is preferred because the piston thus remains stress-free until use, whereby an undesired premature product dispensing is avoided. In principle, it is also possible, however, that the drive member bears against the piston in the delivered state and not for the first time during the dispensing of the product. Insofar as the drive member bears against the piston in the delivery state, the dispensing stroke of the piston corresponds to the dispensing stroke of the drive member.

Needle Guard Sleeve

In embodiments having a needle guard sleeve, it is preferred that the needle guard sleeve act on the second spring to trigger dispensing of the product, wherein the needle guard sleeve can be displaced from the initial position thereof in the proximal direction relative to the housing and along the longitudinal axis of the autoinjector, i.e. contrary to the dispensing direction, more particularly by the actuation stroke. Thereby the second spring is tensioned and dispensing of the product, more particularly the movement of the drive member in the dispensing direction, is preferably released or initiated. The needle guard sleeve is preferably thereby moved from the initial position thereof by the actuation stroke into the actuated position such that the distal end thereof is pressed against the puncture point on the patient, wherein the housing is displaced relative to the needle guard sleeve in the direction of the puncture point so that the needle guard sleeve carries out the actuation stroke relative to the housing. In the process, the needle protruding from the distal end of the needle guard sleeve is also inserted into the puncture point. After dispensing of the product has been finished, more particularly after a brief waiting time such as 3 to 10 seconds, after which a signal has been produced by means of an end signal member, the autoinjector is removed from the puncture point, whereby the needle guard sleeve is displaced by the needle guard stroke relative to the housing from the actuated position into the needle guarding position, more particularly by means of the spring energy stored in the second spring. By removing the autoinjector from the puncture point, the needle is also pulled out of the puncture point.

In certain embodiments, a switching module can be arranged kinematically between the second spring and the needle guard sleeve, wherein the switching module is driven by the needle guard sleeve in the proximal direction when the needle guard sleeve is displaced from the initial position thereof in the proximal direction or into the actuated position, and the needle guard sleeve is displaced in the distal direction if the spring acting on the switching module displaces the switching module in the distal direction. The switching module, or a part thereof, for example a switching sleeve, can be integral with the needle guard sleeve or form-fittingly connected, for example snap-fitted, or can loosely contact the needle guard sleeve. The switching module can be a single part or can comprise multiple parts, wherein a multipart switching module can have at least the switching sleeve and a blocking sleeve. The blocking sleeve can be displaceable relative to the needle guard sleeve and/or the switching sleeve, along the longitudinal axis, for example. For instance, the spring can be supported on the switching sleeve and the switching sleeve can be supported on the needle guard sleeve. Between the blocking sleeve and the switching sleeve, a latching member acting unidirectionally, for example, can be provided, which is formed by the blocking sleeve for example, and engages with the switching sleeve, particularly with a recess or the distal end thereof. The latching member is preferably designed such that the switching sleeve drives the blocking sleeve relative to the housing in the proximal direction via the latching member during travel of the switching sleeve, in particular during the movement of the needle guard sleeve from the initial position into the actuated position, and the switching sleeve is displaced relative to the blocking sleeve into a blocking position during the movement in the proximal direction relative to the housing, in particular during the displacement of the needle guard sleeve from the actuated position thereof into the needle guarding position, wherein, in the blocking position, the latching member, or a different latching member such as the above-mentioned one, blocks a movement of the switching sleeve in the proximal direction relative to the blocking sleeve. This advantageously prevents the needle guard sleeve from being able to be pushed out of the needle guarding position back into the housing for another release of the needle tip.

For example, the switching sleeve can have a first recess, with which the latching member of the switching sleeve releasably engages if the needle guard sleeve is pushed out of the initial position into the actuated position. For example, the switching sleeve can have a second recess, with which the latching member or optionally the other latching member engages when the needle guard sleeve is in the needle guarding position. The first and second recesses can preferably be arranged with a spacing between them along the longitudinal axis that corresponds roughly to the needle guard stroke. A reversal of the arrangement of the recesses and the latching member or latching members is of course also possible, i.e. the at least one latching member can be formed on the switching sleeve and the at least one recess, i.e. the first recess and optionally the second recess, can be formed on the blocking sleeve.

The latching member and optionally the other latching member can be arranged resiliently, in particular each on a resilient arm. The switching sleeve can preferably surround and/or guide the blocking sleeve.

Cap

The autoinjector additionally has a closure cap or a proximal housing part, which can be attached to the proximal end of the housing and forms the proximal end of the autoinjector. The cap or the proximal housing part can preferably create space for the drive spring or the first spring, more particularly the spiral spring. The closure cap or the proximal housing part can be coupled to the housing such that it can be rotated relative to the housing. For example the proximal housing part can be a metering knob or a loading knob with which the spring can be loaded prior to injection. In a preferred embodiment, the closure cap or the proximal housing part can be form-fittingly connected to the housing, but can alternatively be frictionally connected or integrally bonded. It is especially preferable if the cap or the second housing part have detachable and nondetachable connections. The cap or the proximal housing part can preferably be detachably connected to the housing in a first assembly step and can be detached from the housing in a second assembly step for inserting the product container, and be non-detachably connected after insertion of the syringe body. The cap or the proximal housing part is preferably non-releasably interlocked with the housing in the second assembly step. A separate cap or a proximal housing part having detachable and non-detachable interlocking connections has the advantage of facilitating the assembly of the device, wherein at least a part of the components can be installed via the proximal end of the housing for final assembly and detachably fixed to the cap in pre-assembly. After temporary removal of the cap or the proximal housing part in final assembly, the syringe body can be inserted via the proximal end of the housing and the two housing parts can be form fittingly and non-detachably interlocked, or alternatively frictionally connected or integrally bonded.

Start Click

In preferred embodiments, the autoinjector can have a retaining element, on which one end of the second spring, particularly the proximal end of the second spring, can be supported, for example. The spring can alternatively be supported at the proximal end thereof on the housing or an element fixed relative to the housing. The second spring can be supported at the distal end thereof on a housing or an element fixed relative to the housing, for example. The second spring can especially preferably be supported at the distal end thereof on the needle guard sleeve or an element that is displaced along with the needle guard sleeve, particularly during the displacement of the needle guard sleeve relative to the housing. For example, the element can be the switching module, particularly the switching sleeve. The retaining element itself can be fixed relative to the housing or can be arranged displaceably in relation to the housing. The retaining element can have a first engagement element, which engages with the drive member before product dispensing is triggered, whereby the drive member is prevented from moving in the dispensing direction relative to the retaining element and/or the housing. The engagement of the first engagement element with the drive member can be released for dispensing product. If the engagement is released, the drive member is enabled for movement in the dispensing direction. The first spring can displace the drive member in the dispensing direction relative to the retaining element and/or the housing by the dispensing stroke. The drive member can have a recess for the first engagement element of the retaining element, wherein this coupling between the drive member and the retaining element is released if the retaining element, more particularly the first engagement element, has disengaged from the drive member, more particularly the recess of the drive member. In particular, the first engagement element can be released from the engagement with the drive member by displacing the needle guard sleeve by the actuation stroke from the initial position into the actuated position. For example, the first engagement element can be held by the needle guard sleeve or the switching module, particularly the blocking sleeve, in the axially fixed engagement with the drive member if the needle guard sleeve is not in the actuated position thereof or in the initial position. For example, an inner periphery of the needle guard sleeve or of the switching module, particularly the blocking sleeve, can keep the engagement element engaged with the drive member.

By displacing the needle guard sleeve into the actuated position, the needle guard sleeve or the switching module, in particular the blocking sleeve, can allow the first engagement element to disengage from the drive member, in particular by a movement transverse to the longitudinal axis of the autoinjector. For example, a first recess, more particularly for the second engagement element, which recess is formed on the needle guard sleeve or the switching module, more particularly the blocking sleeve, can be arranged relative to the longitudinal axis at the same position as the first element and/or the second engagement element, so that the first engagement element can disengage from the drive member. For example, the drive member can press the first engagement element out of engagement with the drive member if the needle guard sleeve is in the actuated position.

The first engagement element can face radially toward the longitudinal axis, for example, and/or can be arranged on a resilient arm of the retaining element.

The retaining element can, as explained, have a second engagement element that, by the disengaging movement of the first engagement element, can be moved out of the drive member into engagement with the needle guard sleeve or the switching module, more particularly the blocking sleeve. The second engagement element can be arranged on the arm on which the first engagement element is arranged, for example, and/or can point radially away from the longitudinal axis. The first engagement element and the second engagement element can be matched to one another such that the second engagement element already engages axially fixedly with the recess therefor, which is formed by the needle guard sleeve or the switching module, more particularly the blocking sleeve, when the first engagement element has not yet completely disengaged from the drive member. This has the advantageous effect that the axially fixed connection between the retaining element and the needle guard sleeve or the switching module is established before the axially fixed connection between the retaining element and the drive member is released.

Particularly if the second engagement element is in its recess, the drive member can move in the distal direction relative to the retaining element, due in particular to the energy stored in the preloaded first spring. The drive member can prevent the second engagement element from disengaging from the axially fixed engagement with the needle guard sleeve or the switching module, in particular the blocking sleeve, if the drive member moves in the distal direction relative to the retaining element.

Since the axially fixed coupling between the drive member and the retaining element has now been canceled or released, the retaining element can be moved proximally relative to the housing by the second spring. In particular, the blocking sleeve can be moved by a distance between the blocking sleeve and a start signal stop. The second spring can accelerate the retaining element and/or the blocking sleeve over this distance, whereby the blocking sleeve strikes the start signal stop at a speed such that a start impulse is emitted, which generates an acoustic (audible) and/or tactile (tangible) signal.

The start signal stop can be formed by the housing or by an element connected at least axially fixedly and preferably also rotationally fixedly to the housing. For example, this element can be the mechanism holder. The signal stop is preferably arranged along the longitudinal axis of the autoinjector such that it is aligned with the blocking sleeve. This has the effect that the blocking sleeve strikes the start signal stop when the retaining element moves along the longitudinal axis of the autoinjector.

End of Injection Signal

According to the invention, the autoinjector has an end signal stop. As already mentioned, the second spring can exert a spring force acting on the retaining element contrary to the dispensing direction, or in the proximal direction. In particular, the second spring can be supported at the proximal end thereof on the end signal stop, for example.

The spring can therefore preferably fulfill multiple functions, since it exerts force for displacing the needle guard sleeve or the switching module and exerts force on the retaining element for a start signal and for an end signal.

As already mentioned above, the drive member can prevent the second engagement element from disengaging from the needle guard sleeve or the switching module if the drive member moves in the distal direction relative to the retaining element. At the end of the dispensing stroke, the drive member allows the second engagement member to disengage from the needle guard sleeve or the switching module or the blocking sleeve. When the second engagement member has disengaged from the needle guard sleeve or the switching module or the blocking sleeve at the end of dispensing, the retaining element is accelerated contrary to the dispensing direction by the second spring and strikes against the end signal stop.

The end signal stop can be formed by the housing or an element connected at least axially fixedly, preferably also rotationally fixedly, thereto. This element can be the mechanism holder, for example. The end signal stop is preferably arranged along the longitudinal axis of the autoinjector such that it is aligned with the retaining element. This has the effect that the retaining element strikes the end signal stop by a movement along the longitudinal axis of the autoinjector.

Blocking of the Needle Guard Sleeve

Particularly in embodiments in which the distal recess for the second engagement element of the retaining element is formed by the needle guard sleeve or the switching sleeve, in particular the blocking sleeve, it is preferred that the second engagement element disengage from the recess at the end of the dispensing stroke in order to be able to move the needle guard sleeve out of the actuated position into the needle guarding position after administration of the product. To this end, the drive member can have a proximal recess with which the first engagement element can engage while the second engagement element is simultaneously disengaging from its recess. The distal recesses on the blocking sleeve can also form the distal end of the blocking sleeve. It is also possible for the proximal recess on the drive member to function as the proximal end of the drive member.

In embodiments having a switching module that has a switching sleeve and a blocking sleeve, it is preferred that the blocking sleeve engage by means of an inward-facing blocking arm with the housing, or an element fixed relative to the housing such as the mechanism holder, and thus prevents the blocking sleeve from being moved relative to the housing in the distal direction, wherein the switching sleeve and/or the needle guard sleeve can be displaced in the distal direction relative to the blocking sleeve, due in particular to the energy stored in the second spring, by which the needle guard sleeve is moved into the needle guarding position. As already described and only noted for the sake of completeness, the latching member can engage between the blocking sleeve and the switching sleeve to prevent the switching sleeve from being movable in the proximal direction relative to the blocking sleeve. A movement of the blocking sleeve in the proximal direction is preferably prevented in that the blocking sleeve strikes against either the housing or an element fixed relative to the housing such as the mechanism holder.

Syringe Holder

The autoinjector additionally has a product container holder, more particularly a syringe holder, in particular for an autoinjector, in which the product container is not displaceable relative to the housing, or for an autoinjector of the type described above.

The invention assumes a syringe module that is provided especially for use in an autoinjector. In particular, an autoinjector already having such a syringe module can be provided. The syringe module comprises a syringe and a syringe holder. The syringe has a syringe body, a piston and a needle, wherein the needle is mounted non-detachably on a needle holder portion of the syringe, for example, and the piston is arranged displaceably in a cylindrical portion of the syringe body, the syringe body having a tapering portion or region arranged between the cylindrical portion and the needle holding portion. The syringe further comprises a needle guard cap, which can be a soft needle shield, for example, or preferably a rigid needle shield (RNS). A soft needle shield is preferably made from an elastomeric plastic, while a rigid needle shield is formed from a shell of hard plastic in which a sheath made from an elastomeric plastic is arranged. The sheath made from elastomeric material and the shell made from hard plastic together form the rigid needle shield. The needle guard cap, which covers the needle and on which, in particular, a needle holding portion extending conically in the direction of the needle tip is mounted, preferably keeps the needle sterile and protected against dirt. A gap is formed above the tapering portion between the cylindrical portion and the needle guard cap, more particularly the shell made of hard plastic.

The syringe holder has at least one engagement member, more particularly a shoulder, on which the tapering portion of the syringe is supported in the distal direction and that engages with the gap between the needle guard cap and the cylindrical portion. The fact that the tapering portion bears against the at least one shoulder advantageously prevents the syringe from being able to move in the distal direction relative to the syringe holder.

It is preferred that there is or remains a gap between the shoulder and the needle guard cap, so that the needle guard cap is not placed under a load by the shoulder. This advantageously prevents the sterility of the needle from being impaired by unintended displacement of the needle guard cap by means of the shoulder.

In preferred embodiments, the syringe body can have a finger flange at the proximal end thereof, wherein a gap is formed between the finger flange and the syringe body if the tapering portion bears against the shoulder, whereby the finger flange remains substantially stress-free. This advantageously prevents the finger flange from being overloaded and breaking the syringe body.

It is additionally preferred that the syringe holder have at least one retaining member, more particularly a protrusion directed outward, by which the syringe holder can be or is connected axially fixedly to a housing of the autoinjector, and more particularly, is or can be snap-connected thereto.

In preferred embodiments, the syringe holder can have at least one cam, which is arranged resiliently, in particular on an arm and distal to the retaining member, for example. The at least one cam can inhibit or hinder a needle guard sleeve in moving out of its initial position into its actuated position such that, if a limit force exerted onto the needle guard sleeve along the longitudinal axis L of the autoinjector is exceeded, the at least one cam is pressed out of engagement with the needle guard sleeve, whereby the needle guard sleeve can be abruptly displaced relative to the housing into its actuated position.

The housing of the autoinjector can have a retaining portion, for example, which bears against the syringe holder, more particularly an outer surface or an outer periphery of the syringe holder, and prevents the at least one engagement member from moving away from the longitudinal axis transversely to the longitudinal axis. In particular, the retaining portion can be annular and surround the at least one engagement member, preferably two or three or four engagement members, such that at least one engagement member is arranged inside the housing portion. For installing or inserting the syringe in the syringe holder, the syringe holder is disengaged from the retaining portion of the housing. When the syringe has been completely inserted into the syringe holder, more particularly when the at least one engagement member has engaged with the gap between the tapering portion and the needle guard cap, the syringe module or the syringe holder is brought into engagement with the retaining portion such that the at least one engagement member is prevented from disengaging from the tapering portion transversely to the longitudinal axis, more particularly away from or outward from the longitudinal axis.

BRIEF DESCRIPTION OF THE DRAWINGS

FIG. 1 shows an exploded view of an autoinjector according to a particularly preferred embodiment.

FIGS. 2a and 2b show the autoinjector from FIG. 1 in a delivery state, wherein FIGS. 2a and 2b are sectional views running through the longitudinal axis of the device, wherein the sectional views are angularly offset about the longitudinal axis.

FIGS. 3a and 3b show the device and the views from FIGS. 2a and 2b, wherein a needle guard sleeve is in the actuated position.

FIGS. 4a and 4b show the device and the views from FIG. 2a and 2b, wherein a signal that signals the beginning of product dispensing is generated.

FIGS. 5a and 5b show the device from FIGS. 2a and 2b, wherein a drive member is shown at the end of the dispensing stroke.

FIGS. 6a and 6b show the device and the views from FIGS. 2a and 2b, wherein a signal that signals the end of product dispensing is generated.

FIGS. 7a and 7b show the device and the views from FIGS. 2a and 2b, wherein the needle sleeve is in the needle guarding position.

FIGS. 8a-8c show the representation of the rotation member or threaded rod and the drive member and embodiments thereof.

BRIEF DESCRIPTION OF THE DRAWINGS

The autoinjector has a sleeve-like longitudinal housing 2 having a longitudinal axis L, and having a closure cap 12 at the proximal end of the housing, which is form-fittingly connected, axially and rotationally fixed, to the housing 2 and forms the proximal end of the autoinjector. The closure cap 12 is snap-fitted to the housing 2. For this purpose, the closure cap 12 has a catch member 12a, which is snapped into a recess 2a on the housing 2, preferably such that the closure cap 12 is not detachable from the housing 2 or not readily detachable.

In the delivery state (FIGS. 2a and 2b), a pull-off cap 4, which is pulled off or twisted off and removed prior to use, is arranged at the distal end of the autoinjector.

A product container 13 in the form of a syringe is received in the housing 2, immovable—other than during the assembly of the autoinjector—along the longitudinal axis L relative to the housing 2. The product container 13 has a sleeve-like syringe body that surrounds a piston 13b, which bears sealingly against the inner periphery of the syringe body. At the distal end, the syringe body has an injection needle 13a, the distal end of which is formed by the tip and which is, in particular, non-detachably connected to the syringe body. Between the injection needle 13a and the piston 13b, a liquid product, more particularly a medicine, is arranged inside the syringe body, wherein the liquid product is dispensed from the product container 13 through the hollow injection needle 13a by displacement of the piston 13b in a dispensing direction, i.e. in the distal direction or toward the injection needle 13a. At the proximal end, the syringe body has a so-called finger flange, which protrudes radially outward from the outer periphery of the cylindrical syringe body.

The product container 13 is received in a product container holder, referred to as syringe holder 1, in such a manner that the container is secured at least against a movement along the longitudinal axis L in the distal direction relative to the syringe holder 1. The syringe holder 1 is form-fittingly connected, more particularly snap-fitted, to the housing 2, as can best be seen from FIG. 2a. For this purpose, the housing 2 has recesses, with which catch elements, formed here at the proximal end of the syringe holder 1, engage. The syringe holder 1 has at least one inward-protruding shoulder 1b, on which a tapering portion of the product container 13 is supported and is positioned distal to the cylindrical syringe body portion guiding the piston 13b.

To prevent the product container 13 from being able to move in the proximal direction relative to the syringe holder 1, the product container 13 is pressed at the proximal end thereof into engagement with the shoulder 1b by a holder acting on the syringe body. The holder is formed by a retaining spring portion 5c of a mechanism holder 5. The mechanism holder 5 is arranged along the longitudinal axis L, in particular non-displaceably and rotationally fixedly in relation to the housing 2. The sleeve-like mechanism holder 5 can be snap-fitted to the housing 2. Differences in length of the product container 13, which can result from manufacturing tolerances, can be compensated by the retaining spring portion 5c, assuring the firm positioning of the product container 13 on the shoulder 1b.

The product container 13 is arranged in relation to the housing 2 such that the needle tip protrudes distally from the distal end of the housing 2. In the initial or delivery state of the autoinjector, i.e. when the pull off cap 4 is arranged on the autoinjector, the needle 13a is covered by a needle cover cap 14, designed in the example shown as a so-called rigid needle shield familiar to a person skilled in the art, or alternatively as a soft needle shield, in order to protect the needle 13a against contamination and to keep the needle 13a and the medicine sterile. The rigid needle shield 14 is arranged on a needle holding portion of the syringe body, wherein the tapering portion of the syringe body is located between the needle holding portion and the cylindrical portion of the syringe body. The shoulder 1b is arranged between the syringe body and the proximal edge of the rigid needle shield 14, more particularly such that a gap, albeit a small one, is formed between the rigid needle shield 14 and the shoulder 1b in order to prevent the shoulder 1b from exerting a force on the rigid needle shield 14, whereby the sterility of the needle 13a or the liquid product could be endangered, for example. The pull-off cap 4 is detachably snapped to the housing 2 or a needle guard sleeve 3, wherein this snapping is released if the pull-off cap 4 is removed from the housing 2 or the needle guard sleeve 3. The snapping is formed in the example shown by a snapping geometry 3b of the needle guard sleeve 3 and a snap hook 4a of the pull-off cap 4 (FIG. 2b). These snap hooks 4a further secure the pull-off cap 4 against a proximal movement relative to the housing 2 by finding support, fixed relative to the housing, on the housing 2 or on a distal end face on the syringe holder 1. The pull-off cap 4 additionally has at least one snapper 4b, in particular on a snap hook 4a, which engages with a gap between the syringe body, more particularly the tapering region thereof, and the proximal edge of the ridge needle shield 14. When the pull-off cap 4 is removed from the autoinjector, the snapper 4b hooks into the proximal end of the rigid needle shield 14, whereby the rigid needle shield 14 is detached from the product container 13 and removed together with the cover cap 4.

The autoinjector has a needle guard sleeve 3 that can be displaced relative to the housing 2 and along the longitudinal axis L by an actuation stroke $H_B$ (FIGS. 3a and 3b) in the proximal direction into an actuated position in order to trigger dispensing of the product. In the initial position of the needle guard sleeve 3, as shown in FIGS. 2a and 2b, when the pull-off cap 4 has been removed, the distal end of the needle guard sleeve 3 protrudes distally past the needle tip of the needle 13a so that an access to the needle tip is initially prevented. By displacing the needle guard sleeve 3 by the actuation stroke $H_B$, the needle guard sleeve 3 is displaced in the proximal direction sufficiently far that the needle 13a protrudes from the distal end of the needle guard sleeve 3, more particularly by a length that corresponds to the injection depth of the needle into the injection point. The needle 13a should preferably protrude past the distal end of the needle guard sleeve 3 sufficiently that a subcutaneous or intramuscular injection can be performed. In particular, the housing 2 can form a stop 2c (FIG. 3b) against which the needle guard sleeve 3 bears in the actuated position.

After the injection has been finished, the needle guard sleeve 3 can be displaced relative to the housing 2 from the actuated position along the longitudinal axis L by a needle guard stroke $H_N$ in the distal direction into a needle guarding position (FIGS. 7a and 7b). In the needle guarding position, the distal end of the needle guard sleeve 3 protrudes distally past the needle tip, so that access to the needle tip is prevented and the risk of injury is reduced. The needle guard sleeve 3 can be blocked against being pushed back out of the needle guarding position as described below.

The syringe holder 1 has a protrusion 1a that is formed radially outwardly, wherein the protrusion 1a engages with a slot-like recess, arranged between the housing 2 and the syringe holder 1, of the needle guard sleeve 3. In the starting position of the needle guard sleeve 3 (FIGS. 2a and 2b) and/or in the needle guarding position of the needle guard sleeve 3 (FIGS. 7a and 7b), the needle guard sleeve 3, more particularly the proximal end of the slot-like recess, bears against the protrusion 1a, whereby a movement of the needle guard sleeve 3 in the distal direction is prevented. A cam 1c, which is arranged resiliently on the syringe holder 1 and is formed by the syringe holder 1, can engage with this slot-like recess, or alternatively with a different recess of the needle guard sleeve 3. The cam 1c is designed such that, in the attempt to displace the needle guard sleeve 3 from the starting position into the actuated position, the cam 1c initially prevents displacement of the needle guard sleeve 3, whereas the cam 1c is pressed out if the force exerted on the needle guard 3 for sliding back exceeds a defined threshold value, whereby the needle guard sleeve 3 is abruptly displaced back into the actuated position. The needle 13a can thereby be pressed abruptly into the puncture point. In order to insert the needle 13a, or displace the needle guard sleeve 3 into the actuated position, the distal end of the needle guard sleeve 3 is placed on the injection point, the housing 2 then being pressed in the direction of the injection point, the housing 2 being abruptly displaced toward the insertion point, and the needle guard sleeve 3 being displaced into the actuated position relative to the housing 2 if the pressing force exceeds the above-mentioned threshold value.

The housing 2 has an annular retaining portion or annular portion 2b, which in particular surrounds the distal end of the syringe holder 1 annularly and bears against it, whereby the at least one shoulder 1b is engaged with the tapering portion of the syringe body. In the region of the retaining portion 2b, the housing 2 further comprises a translation stop in the form of a retaining shoulder 2e, which prevents the syringe holder 1 from being displaceable in the distal direction relative to the housing 2 if the syringe holder 1 bears against the retaining shoulder 2e. This also advantageously applies to the described variants.

Piston Rod Having a Spring and Threaded Rod

The autoinjector further comprises piston rod or a drive member 7, in particular a sleeve-shaped drive member, which has a thread segment 7b in particular on the inner side thereof (FIG. 8a). The thread segment is shown in FIG. 8a in a detailed view, wherein the thread segment has in particular an oval shape.

A flank 7b' of the thread segment 7b of the drive member 7 can preferably have different pitch angles.

With a variable thread pitch, a different region of the thread segment 7b can be contacted in each case by the thread of a threaded rod 11.

In a helical movement between the threaded rod 11 and the at least one thread segment 7b of the drive member 7, the flank 7b' of the at least one thread segment 7b is screwed on the thread having the variable pitch of the threaded rod, wherein different regions of the flank 7b' contact the thread having the variable pitch.

In a preferred embodiment, the drive member 7 is in particular rotationally fixed relative to the housing 2. Additional preferred embodiments are illustrated in FIG. 8c. As already mentioned, the drive member 7 can have a threaded connection to the housing, or to an element fixed relative to the housing, more particularly the mechanism holder.

The thread on the drive member 7 can have a progressive or a degressive pitch. An appropriate pitch on the drive member 7 is selected, depending on the profile that is desired for the progression of the dispensing force and the pitch of the thread on the rotation member or threaded rod 11. For a profile in which the dispensing force is to remain constant and with a small and constant thread pitch on the threaded rod 11, the drive member 7 has a degressive pitch. That is to say, a small pitch can be selected for the initial region of the dispensing and a large pitch toward the end.

As already mentioned, the autoinjector further comprises a rotation member, in particular a threaded rod 11 (FIG. 8b), the rotation of which has the effect that spring energy is output to the drive member 7, whereby the drive member 7 is moved by a threaded drive in the distal direction. The threaded rod 11 is connected to the first spring 9, which stores the energy necessary for dispensing the product and outputs it when necessary. The threaded rod 11 is coupled to one end of the first spring 9, while the other end of the first spring 9 is connected to the closure cap 12.

The threaded rod 11 has a thread having a variable pitch, wherein the thread has a large pitch in the first region. There is a distance or an acceleration path x between the piston rod and the piston. In order to control the acceleration of the piston rod on the acceleration path x or to decelerate the piston and reduce the risk of glass breakage, a thread start path E having a large pitch for the beginning of the piston rod movement is provided on the threaded rod 11. The axial portion x' of the thread start path E is preferably larger than the acceleration path x. In addition, the axial forces that arise in a storage position due to thread transmission, particularly from the spring torque due to the thread transmission, can be kept small by a large pitch on the threaded rod 11.

For a dispensing profile having a constant dispensing force, the thread or the thread pitch varies over the length of the threaded rod 11.

The pitch is degressive and has a pitch that constantly becomes smaller, whereby the decrease of the spring torque during the dispensing can be compensated, wherein the largest thread pitch, in the region E, is not self-locking.

The threaded rod 11 is axially fixed in relation to the housing 2 and can be supported axially fixedly at least in a distal direction on the mechanism holder 5.

Due to the release of the drive member 7, the first spring 9 is allowed to move the drive member 7 in the distal direction. The first spring 9 is a spiral-shaped spring that is preloaded in the initial or delivery state of the autoinjector with sufficient energy that it can dispense the product contained in the product container 13 from the product container 13 completely, in particular by rotating the threaded rod 11 and displacing the drive member 7 by a dispensing stroke $H_A$. In the delivery state of the device, there is a space between the piston 13b and the distal end of the drive member 7, so that the drive member 7 only strikes the piston 13b during the execution of the dispensing stroke $H_A$ and drives it in the dispensing direction.

The autoinjector further comprises a retaining element 6, which has two arms 6c in the present example, wherein a first engagement element 6a and a second engagement element 6b are arranged on each arm 6c. The first engagement element 6a radially faces the longitudinal axis L, while the second engagement element 6b radially faces away from the longitudinal axis L. The first engagement element 6a engages with a recess 7a that is formed by the drive element 7, whereby a movement of the drive member 7 relative to the retaining element 6 in the distal direction or in the dispensing direction is prevented. This keeps the first spring 9 in a loaded state.

The autoinjector has a switching module 8, 15, which has a switching sleeve 15 and a blocking sleeve 8 surrounded by the switching sleeve 15. In the delivery state of the device, the first engagement element 6a is kept engaged with the recess 7a by the inner periphery of the locking sleeve 8, which contacts the second engagement element 6b.

The switching sleeve 15 is connected to the proximal end 3a of the needle guard sleeve 3, or at least bears against the proximal end 3a of the needle guard sleeve 3. A second spring 10, which preferably surrounds the switching sleeve 15 and the blocking sleeve 8 at least in part, is supported at the distal end thereof on the switching sleeve 15. A part of the switching sleeve 15 is therefore arranged between the needle guard sleeve 3 and the distal end of the second spring 10. The second spring 10 is a spring made from metal that acts as a compression spring and is constructed as a coil spring. The second spring 10 is supported at the proximal end thereof on the retaining element 6, more particularly on a protrusion 6e, which engages axially displaceably and nonrotatably with the housing 2. The second spring 10 thus also surrounds the mechanism holder 4 at least in part, preferably completely.

The switching member 15 has a recess 15a, with which a latching member 8a of the locking sleeve 8 engages. The latching member 8a has a sawtooth shape and protrudes radially away from the longitudinal axis L. The latching member 8a is resiliently arranged on an arm that is formed by the blocking sleeve 8. By displacing the switching sleeve 15 in the proximal direction, the blocking sleeve 8 is driven in the proximal direction via the engagement of the latching member 8a.

By displacing the needle guard sleeve 3 into the actuated position, the switching sleeve 15 is likewise driven by the actuating stroke $H_B$, whereby the second spring 10 is tensioned. If the needle guard sleeve 3 is not completely displaced into the actuated position, the second spring 10 can displace the switching sleeve 15 and the needle guard sleeve 3 back into the initial position, wherein the blocking sleeve 8 is driven by the switching sleeve 15 by means of the engagement of the latching member 8a.

To administer the product from the product container 13, the pull-off cap 4 is removed from the autoinjector together with the rigid needle shield 14. The distal end of the needle guard sleeve 3 is placed on the insertion point of a patient, wherein the housing 2 is displaced toward the insertion point, whereby the needle guard sleeve 3 is moved out of the initial position thereof by the actuating stroke $H_B$ in the proximal direction relative to the housing 2 into the actuated position. Thereby the second spring 10 is tensioned, wherein the switching sleeve 15 is driven by the actuating stroke $H_B$ by means of the needle guard sleeve 3. The blocking sleeve 8 has a recess or a distal end 8b, which is brought to the position of the second engagement element 6b by displacement of the blocking sleeve 8 by the actuating stroke $H_B$ along the longitudinal axis L, as shown in FIGS. 3a and 3b. Thereby the first engagement element 6a is moved out of the engagement with the drive member 7 by a movement transverse to and away from the longitudinal axis L while simultaneously the second engagement element 6b is moved into engagement with the blocking sleeve 8, more particularly the recess 8b thereof. Thereby the drive member 7 is released for the movement by the dispensing stroke $H_A$ in the dispensing direction.

Since the axially fixed coupling between the drive member 7 and the retaining element 6 is now canceled or released, the retaining element 6, which can be moved at least slightly relative to the housing 2 and along the longitudinal axis L, is moved by the second spring 10 in the proximal direction, wherein the retaining element 6, by means of the engagement of the second engagement element 6b with the recess 8b, drives the blocking sleeve 8 by a start signal stroke Hs (FIG. 3b), whereby the blocking sleeve 8 strikes against a start signal stop 5a formed by the mechanism holder 5 and thereby outputs an acoustic and/or tactile signal that signals to the user of the device that the product dispensing has begun. Due to the displacement of the blocking sleeve 8 by the actuating stroke $H_B$, the latching member 8a and thus also a blocking arm 8c, which is mounted on the resilient arm of the blocking sleeve and protrudes in a sawtooth shape radially to the longitudinal axis L, is released for a movement transverse to and toward the longitudinal axis L, because the mechanism holder 5 has a recess 5d, which permits such a movement of the latching member 8a when the blocking sleeve 8 has been displaced by the actuating stroke $H_B$ or when the needle guard sleeve 3 is in the actuated position thereof.

Because the second engagement member 6b is still in the recess 8b of the blocking sleeve 8, the retaining element 6 is prevented thereby from moving further in the proximal direction relative to the housing 2 or the blocking sleeve 8. The second engagement member 6b is held by the outer periphery of the drive member 7 in engagement with the recess 8b (FIG. 4a) when the drive member 7 is moved by the dispensing stroke $H_A$ thereof.

At the end of the dispensing stroke $H_A$, the drive member 7 releases the first engagement member 6a for a movement, in particular toward the longitudinal axis L, whereby the second engagement member 6b is moved out of the engagement with the recess 8b of the blocking sleeve 8, such that the second spring 10 accelerates the retaining element 6 contrary to the dispensing direction, i.e. in the proximal direction, so that an acoustic and/or tactile signal is generated when the retaining element 6 strikes against the end signal stop 5e.

As can be best recognized from FIG. 5b, the engagement of the blocking arm 8c with the first recess 5d of the mechanism holder continues, whereby a movement of the blocking sleeve 8 in the distal direction relative to the housing 2 is prevented.

By removing the autoinjector from the injection point, the second spring 10 can move the switching sleeve 15 and the needle guard sleeve 3 by the needle guard stroke $H_N$ (FIGS. 7a and 7b) out of the actuated position into the needle guarding position, wherein the latching member 8a is pressed out of the engagement with the recess 15a, wherein the switching sleeve 15 moves in the distal direction relative to the blocking sleeve 8. When the needle guard sleeve 3 is in the needle guarding position thereof, the latching member 8a snaps together with the switching sleeve 15, wherein the latching member 8a prevents the needle guard sleeve 3 from being pushed back again into the actuated position thereof. In the attempt to push the needle guard sleeve 3 out of the needle guarding position back into the actuated position, the switching member 15 strikes against the latching member 8a, which prevents the movement of the needle guard sleeve 3 into the actuated position. The blocking sleeve 8 is axially supported on the start signal stop 5a of the mechanism holder 5 for this purpose.

What is claimed is:

1. An autoinjector, comprising:
    a first spring, wherein the first spring is preloaded for dispensing a product from the autoinjector; and
    a rotation member operatively coupled to a drive member, wherein the drive member is sleeve-shaped and adapted to act on a piston of a product container, and wherein the sleeve-shaped drive member comprises a thread or a thread segment on an inner side and the rotation member comprises a thread or thread segment on an outer side to thereby couple the rotation member with the drive member,
    wherein the first spring acts on the rotation member such that the rotation member is set into rotation to cause displacement of the drive member for dispensing the product, and
    wherein the thread or thread segment of the rotation member or the drive member comprises a variable pitch.

2. The autoinjector of claim 1, wherein the first spring is a torsion spring or a rotational spring, that stores the energy necessary for dispensing the product.

3. The autoinjector of claim 1, wherein the first spring is a spiral spring.

4. The autoinjector of claim 1, wherein the first spring is axially fixedly mounted in a housing of the autoinjector.

5. The autoinjector of claim 1, wherein the rotation member is coupled at one end to the first spring, while the other end of the first spring is connected to a different element that is axially or rotationally movable relative to a housing of the autoinjector.

6. The autoinjector of claim 1, wherein the rotation member is coupled at one end to the first spring, while the other end of the first spring is connected to a housing or to an element that is fixed relative to the housing.

7. The autoinjector of claim 1, further comprising a second spring, which exerts a spring force on a retaining element acting oppositely to a dispensing direction.

8. The autoinjector of claim 7, the retaining element is coupled to the drive member, and wherein the coupling between retaining element and drive member can be released and the retaining element can be accelerated by means of the second spring opposite to the dispensing direction and relative to the drive member or a housing of the autoinjector.

9. The autoinjector of claim 1, wherein the drive member is rotationally fixed relative to a housing of the autoinjector.

10. The autoinjector of claim 1, further comprising a product container in form of a syringe that has a container body, and wherein an injection needle is fixedly arranged at a distal end of the body.

11. The autoinjector of claim 10, wherein the product container is displaceably arranged in a housing of the autoinjector in a distal direction relative to the housing for automatic insertion.

12. The autoinjector of claim 1, wherein the variable pitch has various pitch angles, wherein the pitch varies along a length of the rotation member or the drive member.

13. The autoinjector of claim 1, wherein a flank of the at least one thread segment of the drive member or of the rotation member comprises different pitch angles.

14. The autoinjector of claim 1, wherein the rotation member comprises a thread start having an axial portion, and a distance between the drive member and a piston defines an acceleration path, wherein the axial portion is larger than the acceleration path.

15. The autoinjector of claim 1, wherein the thread or thread segment having the variable pitch comprises at least one region having a continuous pitch variation or/and a pitch variation of the thread having the variable pitch is discontinuous.

16. The autoinjector of claim 1, wherein the thread or thread segment having the variable pitch comprises a degressive thread pitch, whereby a decrease of a spring torque of the first spring during the dispensing can be compensated.

17. The autoinjector of claim 1, wherein the drive member comprises a first threaded connection to the rotation member and a second threaded connection to a housing of the autoinjector or an element fixed relative to the housing.

18. The autoinjector of claim 1, wherein the rotation member is axially fixed in relation to a housing of the autoinjector.

* * * * *